US007227013B1

(12) United States Patent
Matzuk et al.

(10) Patent No.: US 7,227,013 B1
(45) Date of Patent: Jun. 5, 2007

(54) GROWTH DIFFERENTIATION FACTOR-9 REGULATORY SEQUENCES AND USES THEREFOR

(75) Inventors: Martin Matthew Matzuk, Pearland, TX (US); Julia Andrea Elvin, Houston, TX (US)

(73) Assignee: Metamorphix, Inc., Savage, MD (US)

( * ) Notice: Subject to any disclaimer, the term of this patent is extended or adjusted under 35 U.S.C. 154(b) by 0 days.

(21) Appl. No.: 10/018,638

(22) PCT Filed: Mar. 31, 1999

(86) PCT No.: PCT/US99/07185

§ 371 (c)(1), (2), (4) Date: Jul. 15, 2002

(87) PCT Pub. No.: WO99/50406

PCT Pub. Date: Oct. 7, 1999

(51) Int. Cl.
*C07H 21/04* (2006.01)
*C12N 15/63* (2006.01)

(52) U.S. Cl. .................. 536/24.1; 536/23.1; 435/320.1

(58) Field of Classification Search ............... 536/23.1, 536/24.1; 435/320.1, 325
See application file for complete search history.

(56) References Cited

U.S. PATENT DOCUMENTS 5,614,396 A 3/1997 Bradley et al. .......... 435/172.3
5,821,056 A 10/1998 Lee ............................... 435/6

FOREIGN PATENT DOCUMENTS

WO WO 95/06118 A1 3/1995
WO WO 97/19180 A2 5/1997
WO WO 97/19180 A3 5/1997

OTHER PUBLICATIONS

EMBL database acc. No. AA388141; vb59g09.r1 Ko mouse embryo 11 5dpc *Mus musculus* cDNA clone IMAGE:761344 5', mRNA sequence.

EMBL database acc. No. AA035964: mi70f04.r1 Soares mouse embryo NbME13.5 14.5 *Mus musculus* cDNA clone IMAGE:468895 5' similar to SW:UCR7_BOVIN P13271 Ubiquinol-Cytochrome C Reductase 9.5 KD Protein ;, mRNA sequence.

Bodensteiner, K.J. et al. Molecular cloning of the ovine growth/fifferentiaton factor-9 gene and expression of growth/differentiation factor-9 in ovine and bovine ovaries. *Biol. Reprod.* Feb. 1999;60(2):381-6.

Carabatsos, M.J. et al. Characterization of oocyte and follicle development in growth differentiation factor-9-deficient mice. *Dev. Biol.* Dec. 15, 1998;204(2):373-84.

Casadaban, M.J. et al. Analysis of gene control signals by DNA fusion and cloning in *Escherichia coli. J. Mol. Biol.* Apr. 1980;138(2):179-207.

Dong, J. et al. Growth differentiation factor-9 is required during early ovarian folliculogenesis. *Nature.* Oct. 10, 1996;383(6600):531-5.

Dube, J.L. et al. The bone morphogenetic protein 15 gene is X-linked and expressed in oocytes. *Mol. Endocrinol.* Dec. 1998;12(12):1809-17.

Fitzpatrick, S.L. et al. Expression of growth differentiation factor-9 messenger ribonucleic acid in ovarian and nonovarian rodent and human tissues. *Endocrinology.* May 1998;135(5);2571-8.

Garver, R.I. Jr. et al. Strategy for achieving selective killing of carcinomas. *Gene Ther.* Jan. 1994;1(1):46-50.

Hayashi, M. et al. Recombinant growth differentiation factor-9 (GDF-9) enhances growth and differentiation of cultured early ovarian follicles. *Endocrinology.* Mar. 1999;140(3):1236-44.

Incerti, B. et al., Structure of the mouse growth/differentiation factor 9 gene. *Biochim. Biophys. Acta.* May 26, 1994;1222(1):125-8.

Liang, L.-F. et al. FIGα, a germ cell specific transcription factor involved in the coordinate expression of the zona pellucida genes. *Development.* Dec. 1997;124(24):4939-47.

Lira, S.A. et al. *cis*-Acting DNA elements involved in oocyte-specific expression of mouse sperm receptor gene *mZP3* are located close to the gene's transcription start site. *Mol. Reprod. Dev.* Dec. 1993;36(4):494-9.

McGrath, S.A. et al. Oocyte-specific expression of growth/differentiation factor-9. *Mol. Endocrinol.* Jan. 1995;9(1):131-6.

McPherron, A.C. et al. GDF-3 and GDF-9: two new members of the transforming growth factor-β superfamily containing a novel pattern of cysteines. *J. Biol. Chem.* Feb. 15, 1993;268(5):3444-9.

Millar, S.E. et al. Oocyte-specific factors bind a conserved upstream sequence required for mouse zona pellucida promoter activity. *Mol. Cell. Biol.* Dec. 1991;11(12):6197-204.

Sauer, B. Inducible gene targeting in mice using the Cre/*lox* systems. *Methods.* Apr. 1998;14(4):381-92.

Zinkel, S.S. et al. Indentification of a negatie regulatory element that inhibits c-*mos* transcription in somatic cells. *Mol. Cell. Biol.* May 1992;12(5):2029-36.

Fitzpatrick, S.L., *et al.* "Expression of growth differentiation factor-9 messenger ribonucleic acid in ovarian and nonovarian rodent and human tissues." *Endocrinology.*May 1998; 139(5):2571-8.

*Primary Examiner*—Celine Qian
(74) *Attorney, Agent, or Firm*—Amy E. Mandragouras, Esq.; Lahive & Cockfield, LLP.

(57) ABSTRACT

Isolated GDF-9 regulatory sequences are disclosed, as well as methods of using the sequences to modulate tissue-specific expression of genes. The GDF-9 regulatory sequences include, for example, enhancer and promoter elements that naturally drive transcription of GDF-9 in specific tissues. The GDF-9 regulatory sequences can be derived from the untranscribed upstream (e.g., first 10 kilobases) and downstream regions, and transcribed, untranslated regions of a GDF-9 gene.

2 Claims, 7 Drawing Sheets

Figure 1:
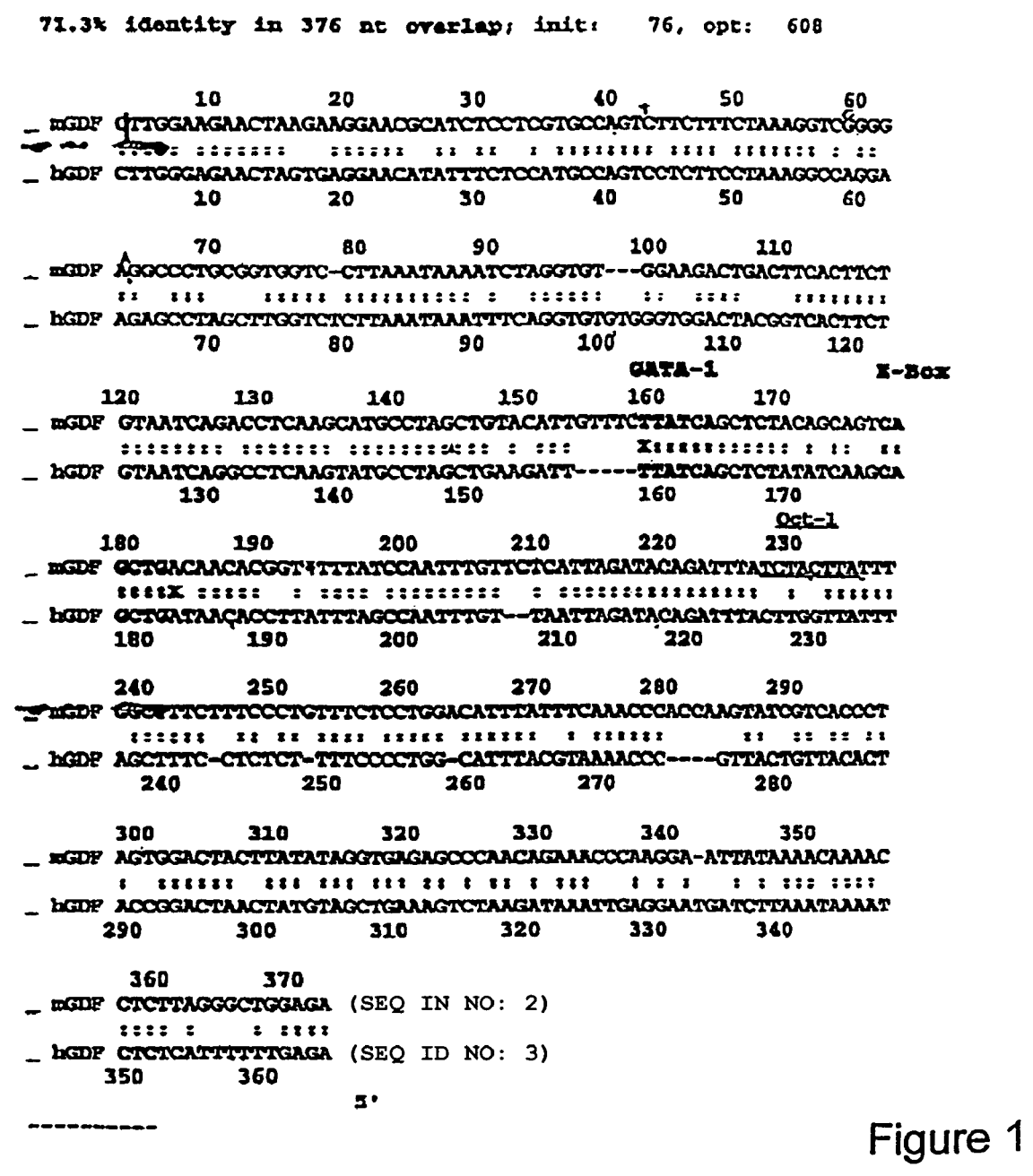

71.3% identity in 376 nt overlap; init: 76, opt: 608

```
          10        20        30        40        50        60
mGDF CTTGGAAGAACTAAGAAGGAACGCATCTCCTCGTGCCAGTCTTCTTTCTAAAGGTCGGGG
hGDF CTTGGGAGAACTAGTGAGGAACATATTTCTCCATGCCAGTCCTCTTCCTAAAGGCCAGGA
          10        20        30        40        50        60

          70        80        90         100       110
mGDF AGGCCCTGCGGTGGTC-CTTAAATAAAATCTAGGTGT---GGAAGACTGACTTCACTTCT
hGDF AGAGCCTAGCTTGGTCTCTTAAATAAATTTCAGGTGTGTGGGTGGACTACGGTCACTTCT
          70        80        90       100       110       120
                                              GATA-1             E-Box
    120       130       140       150       160       170
mGDF GTAATCAGACCTCAAGCATGCCTAGCTGTACATTGTTTCTTATCAGCTCTACAGCAGTCA
hGDF GTAATCAGGCCTCAAGTATGCCTAGCTGAAGATT-----TTATCAGCTCTATATCAAGCA
        130       140       150            160       170
                                                     Oct-1
    180       190       200       210       220       230
mGDF GCTGACAACACGGTTTTTATCCAATTTGTTCTCATTAGATACAGATTTATCTACTTATTT
hGDF GCTGATAACACCTTATTTAGCCAATTTGT--TAATTAGATACAGATTTACTTGGTTATTT
     180       190       200         210       220       230

     240       250       260       270       280       290
mGDF GGCTTTCTTTCCCTGTTTCTCCTGGACATTTATTTCAAACCCACCAAGTATCGTCACCCT
hGDF AGCTTTC-CTCTCT-TTTCCCCTGG-CATTTACGTAAAACCC----GTTACTGTTACACT
       240         250       260       270           280

     300       310       320       330       340       350
mGDF AGTGGACTACTTATATAGGTGAGAGCCCAACAGAAACCCAAGGA-ATTATAAAACAAAAC
hGDF ACCGGACTAACTATGTAGCTGAAAGTCTAAGATAAATTGAGGAATGATCTTAAATAAAAT
    290       300       310       320       330       340

      360       370
mGDF CTCTTAGGGCTGGAGA (SEQ IN NO: 2)
hGDF CTCTCATTTTTTGAGA (SEQ ID NO: 3)
    350       360
```

3.3 kb 5' Sequence
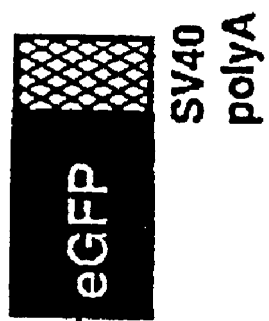
(Expected Transcript Size - ~1kb)
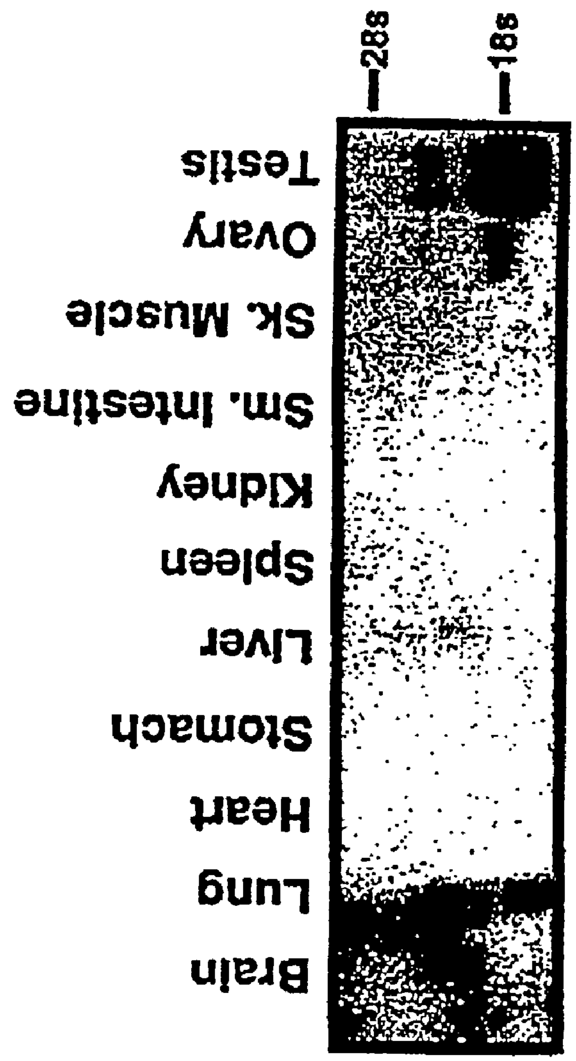
Line 2
Figure 4

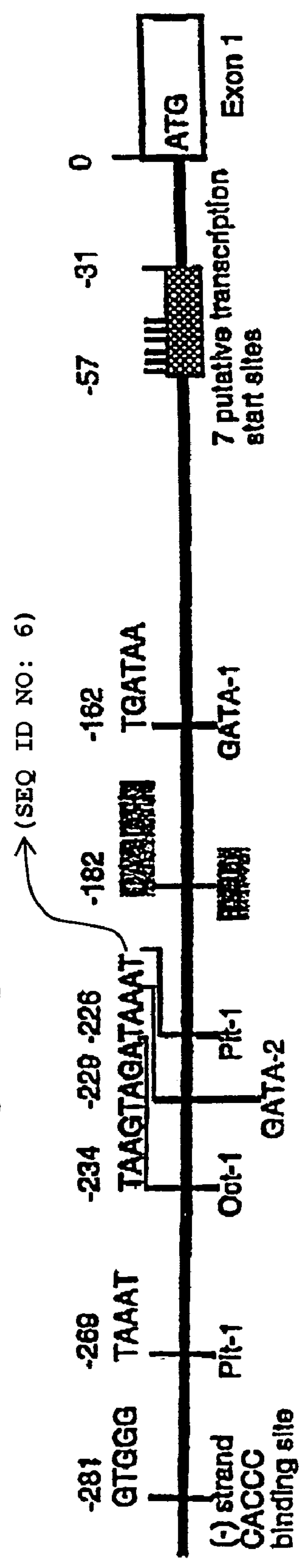
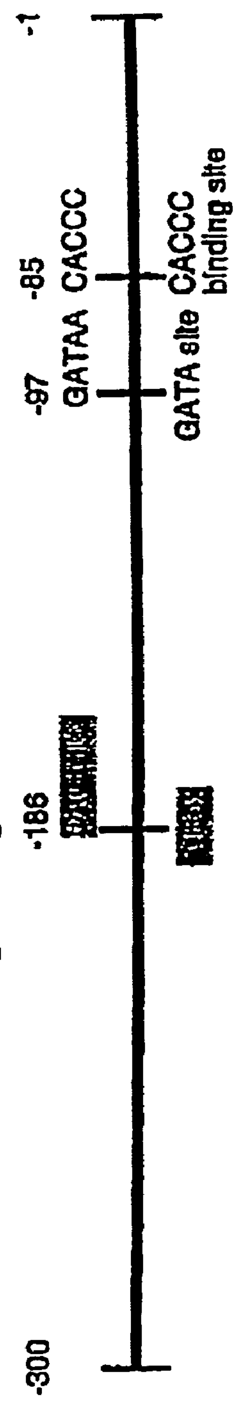
Figure 6

```
                              SEQUENCE LISTING

<160> NUMBER OF SEQ ID NOS: 6

<210> SEQ ID NO 1
<211> LENGTH: 3379
<212> TYPE: DNA
<213> ORGANISM: Mus musculus

<400> SEQUENCE: 1

atgccttgga agaactaaga aggaacgcat ctcctcgtgc cagtcttctt tctaaaggtc     60

ggggaggccc tgcggtggtc cttaaataaa atctaggtgt ggaagactga cttcacttct    120

gtaatcagac ctcaagcatg cctagctgta cattgtttct tatcagctct acagcagtca    180

gctgacaaca cggttttatc caatttgttc tcattagata cagatttatc tacttatttg    240

gctttctttc cctgtttctc ctggacattt atttcaaacc caccaagtat cgtcacccta    300

gtggactact tatataggtg agagcccaac agaaacccaa ggaattataa aacaaaacct    360

cttagggctg gagatgtgac tgcagaagta ttaggtttat tttttcctct tgattcatcg    420

tctatctcca cagctcccac gtccaggtgg ttagaataac tgatggctta ctgcacagtg    480

aatcagagaa acaaagtcac aatgggttct gaaattccag tgatgttagg ctgttcagcc    540

tgtccaggtg gcttagtaga ggggttgtaa agttggccca agacaacagc tacttgcaat    600

gtgctttgaa aaaggacatc agggcccagg tgtagaggtt cacgccttta atcccagcat    660

tcaggagaca caggcaggtg gatctctgtg gattcaagcc agcctggtct atatagagag    720

ttctaggaca gtcagagcta cataattttg agagacccca tctcaaaata aaaagaggac    780

atcaccttta actttgagca attaaaacat acaatgtctt ggggccagaa agatgatgga    840

tgacctggca gttaagggca ctggttgctc ttcttagaac aaccatttat agctccactt    900

ccaggggggag ccaatgcctt tctcgggcat ccttaggaat acaaaaacac ccattataaa    960

atgaaaataa acaattaaaa aaaagccaca atatctagct ggaatggcaa gatagcaact   1020

tgccgccaag cctaacgacc aaaagtcatc cagtcctaaa ggatcaagct tattaagctt   1080

gatcctaact tcaacccctg tgatccacag agaaaaaggg agaagagact tctacagctc   1140

gtcttctgac ctacacccct agcacttaca taccaaatac atattttaaa atgtagtgac   1200

agtacaatat cctgatgccc ttgttttggt ctacaattca cttgactata ctttggttga   1260

aaaatcttga gacatcagca aatgcaatta aatagacatc gtatttattc tttaaccaac   1320

cacccagatg gcagaaatca ggacagtgtt ttagtccttg attaaagtat ttgtgtcccg   1380

gccttggagg tgagatcaag ctagataatg tttaaggaaa atgggggcag ggtggaagtg   1440

ggggggagaa tgtgcagtgc accatgaaag gctatctagc accccttgga aggagactat   1500

ctcttgggag aaagtcaaaa cacactaatg acacaggata aaaaaaaaat cagtttgccc   1560
```

-continued

```
agcaccagat agataaggct gaatctcttg caaaactgaa ctcaccgcca aactgcccca   1620

gtttgaattg ccaaattatt tacagcccag tttaaccctt tacagccctg agaggaggag   1680

aaagggcggt gagtcccaca ggataatatt agctaggaga atgaatgcac tttagagaaa   1740

acataacagt tccttagaga gtggggtctg ggtttgatga cacactcagc ccaaacccac   1800

cactttctcc ttggctccca tcaccattat gtgcgtctga caaactgcca catcgttcgt   1860

ggctgaactg ggagaaacgt ttatgtcaca tcttggacaa gtctacagcc tgccatggct   1920

tgtaggcagt gtgtaccaaa gctctagatc cgtgtcctta attttgtact gtggtcagtg   1980

aaggcccttt tggttatgag gaccacatat acctggtgga gagtaaggga cagcagaaga   2040

acgaggagaa caagtctttt tgttttttct ttttaatttt tgagcagctg ccggctgtta   2100

tgcaaaggcc tggtactgag cggaaaggac cgcctcttgg aacacccagg tgctcctaag   2160

cacgcccatc acctaatccg cgccccatga cctataggcc ccgccccgtg cacttctcga   2220

cgggggacct tacggacgta tccacctaag atccccaggg tggctaataa gccccgccca   2280

cttgcttggc acccttccca ccaagccacc attcctcttc aagccccgcc ccttggcaac   2340

atcaacctct cccgtgcgtt cactacttac cgtaagccca caagcacctc tataagcccc   2400

acccacgtgt cgctagaagc gcctctaagc tccgcccagc ctcttggtat ggtcctttcc   2460

ggctacacga aggtcaggcc acgcccactc aggtcaactg acaatttttt ttttgagtct   2520

ccccccttgag atcgaaagaa aatggtagtt cccggaaatg acttcacgtt ctctaggctc   2580

ggcttccgct cctcccggaa gtgacgggcg aaagccggct cagagctctg gaggtagagg   2640

tgaccgatcc tgggggtcgg tgttaggccg tgggaggttt ttcgcgagac tgagccacgc   2700

gtctatcttc tgtcccaggg ccgcccagga attcgacatg ggccgcgagt ttgggaacct   2760

ggcgcggata cggcacgtga tctcctacag cttgtcgccc tttgagcagc gcgccttccc   2820

aagctatttc agcaaaggca tccccaacgt gtgcgccgca ctcgcgagcg catcctgcgc   2880

gtggcgccgc gtgagtgcgg ggcgggcggg gtacagccgc gcacctctcc ttccgacgcc   2940

ctcgcggggc agacgtggag gagttcttat catatcgaaa tgactggcct aaggtcactt   3000

gggtgactcc aacggctccc tctgaggtca tcgctggcca ctatctgtga tgaaaggctg   3060

atgcaatcag tgtcttgtgt tagatgtgcg gccgattttg ctgtcggttt catggcattg   3120

tgaatatccg tgaaggtgca cttaaatttg atggagaggt tgaggcccga tcttgctgta   3180

gaagccaggc tggccttaaa cttgagattt tactgccctc tcctcgggac tgttggctgg   3240

aattgtaggc atgccgccag cacaacagta ctttttaaaa tggtgaagat tatgttaggt   3300

aaattccgtg attttttttt ttttaatttg gtgttaacta ggaaagcgaa ggccacatct   3360

tcctgggctg atatcaagc                                                 3379
```

```
<210> SEQ ID NO 2
<211> LENGTH: 370
<212> TYPE: DNA
<213> ORGANISM: Mus musculus

<400> SEQUENCE: 2

cttggaagaa ctaagaagga acgcatctcc tgctgccagt cttctttcta aaggtcgggg     60

aggccctgcg gtggtcctta aataaaatct aggtgtggaa gactgacttc acttctgtaa    120

tcagacctca agcatgccta gctgtacatt gtttcttatc agctctacag cagtcagctg    180

acaacacggt tttatccaat ttgttctcat tagatacaga tttatctact tatttggctt    240

tctttccctg tttctcctgg acatttattt caaacccacc aagtatcgtc accctagtgg    300
```

-continued

```
actacttata taggtgagag cccaacagaa acccaaggaa ttataaaaca aaacctctta    360

gggctggaga                                                           370


<210> SEQ ID NO 3
<211> LENGTH: 362
<212> TYPE: DNA
<213> ORGANISM: Homo sapiens

<400> SEQUENCE: 3

cttgggagaa ctagtgagga acatatttct ccatgccagt cctcttccta aaggccagga     60

agagcctagc ttggtctctt aaataaattt caggtgtgtg ggtggactac ggtcacttct    120

gtaatcaggc ctcaagtatg cctagctgaa gattttatca gctctatatc aagcagctga    180

taacacctta tttagccaat ttgttaatta gatacagatt tacttggtta tttagctttc    240

ctctcttttc ccctggcatt tacgtaaaac ccgttactgt tacactaccg gactaactat    300

gtagctgaaa gtctaagata aattgaggaa tgatcttaaa taaaatctct catttttttga    360

ga                                                                   362


<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4

ttcttcaagg gatcccactt tcccag                                          26


<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 5

ctgggaagtg ggatccctgg aagaa                                           25


<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: synthetic
      primer

<400> SEQUENCE: 6

taagtagata aat                                                        13
```

GROWTH DIFFERENTIATION FACTOR-9 REGULATORY SEQUENCES AND USES THEREFOR

FIELD OF THE INVENTION

The invention relates to tissue-specific regulatory elements derived from GDF-9 genes, as well as methods of identifying and using the regulatory elements to control gene expression in selected tissues.

BACKGROUND OF THE INVENTION

Growth differentiation factor 9 (GDF-9) is a recently-identified member of the TGFβ superfamily, which encompasses a large group of growth and differentiation factors that play important roles in regulating embryonic development and in maintaining tissue homeostasis in adult mammals. These factors are synthesized as pre-propeptides, forming dimers in the mature, secreted form. In this dimeric state, GDF proteins are able to interact with various cell surface receptors, thereby modulating a variety of cellular processes. Several TGFβ family members have been found to have tissue-specific expression related to the function of the factor. For example, GDF-8, a negative regulator of skeletal muscle growth, is specifically expressed in cells from skeletal tissue (McPherron, A. C., et al., Nature 387: 83–90, 1997).

The precise function of GDF-9 remains unclear, but the distribution of its gene product is known to be restricted to only a few tissues, particularly the ovary (and in the testes and the hypothalamus at very low levels). In humans, expression is also observed in the pituitary and placenta (Fitzpatrick et al., Endocrinology 139: 2571–2578, 1998). Studies in transgenic mice have found that disruption of the GDF-9 gene results in the prevention of normal follicular development beyond an early stage, resulting in infertility in females (Dong et al., Nature 383: 531–535, 1996; Carabatsos et al., Developmental Biology 204: 373–384, 1998). No data is currently available about the role of GDF-9 in the testes, but male GDF-9-deficient mice exhibit normal fertility.

SUMMARY OF THE INVENTION

The present invention provides isolated GDF-9 regulatory sequences, and methods of using these nucleotide sequences to modulate tissue-specific expression of genes. GDF-9 regulatory sequences of the invention include, for example, enhancer and promoter elements that naturally drive transcription of GDF-9 in specific tissues, and repressor sequences which naturally inhibit GDF-9 in other tissues.

In one embodiment, the GDF-9 regulatory sequences are derived from the 5' or 3' flanking regions of a GDF-9 gene, or from an intron of a GDF-9 gene. In a particular embodiment, the regulatory sequences are derived from the first 10 kilobases of DNA immediately 5' of the transcription start site of a GDF-9 gene, such as a mammalian GDF-9 gene (human or non-human), or an exon of the gene (e.g., mouse exon 1 and 2), or an intron of the gene, or the first 1 kilobase of 3' flanking region of the gene. In another embodiment, the GDF-9 regulatory sequences are derived from the first 3.3 kilobases of DNA immediately 5' of the coding sequence of a GDF-9 gene. For example, the sequences can be derived from the 3.3 kilobase regulatory region from the mouse GDF-9 gene (mGDF-9) having the nucleotide sequence of SEQ ID NO:1. In another embodiment, the GDF-9 regulatory sequences are derived from the first 300 base pairs of DNA immediately 5' of the coding sequence of a GDF-9 gene. In still another embodiment, the GDF-9 regulatory sequences are derived from the region from 3.3 kilobases to 10 kilobases immediately 5' of the coding sequence of a GDF-9 gene.

The invention also includes isolated polynucleotides which comprise or which are derived from the aforementioned GDF-9 regulatory regions, as well as variants and homologies thereof. For example, oocyte-specific and testis-specific control elements are provided which can, for example, be operatively linked to a gene to modulate expression of the gene in these or other selected tissues.

Accordingly, in another aspect, the present invention provides an expression vector containing one or more of the aforementioned isolated GDF-9 regulatory sequences, optionally linked to a gene of interest. The gene can be GDF-9 itself, or can be a gene whose product is desired to be under the control of one or more GDF-9 regulatory elements (e.g., a therapeutic gene or a reporter gene).

In another aspect, the invention provides a cell or tissue transfected to contain one or more of the aforementioned isolated polynucleotides. The cell can be, for example, a cell from the oocyte, testis, placenta, hypothalamus or pituitary.

In yet another aspect, the invention provides methods for obtaining or controlling (i.e., modulating) tissue-specific expression of a gene. The gene can be an endogenous gene or an exogenous gene (e.g., a transgene). In one embodiment, the method involves operatively linking one or more GDF-9 regulatory elements of the invention to a gene and then introducing (e.g., via microinjection) the resulting gene construct into a cell of a selected tissue, such as a tissue in which GDF-9 is naturally expressed (e.g., oocytes, testis, or hypothalamus). GDF-9 regulatory elements of the invention can be used both to upregulate gene expression in such tissues, and to downregulate (e.g., repress) gene expression in such tissues.

In yet another aspect, the invention provides a method for identifying tissue-specific regulatory elements derived from a GDF-9 gene. This can be achieved by, for example, comparing expression levels of a gene (e.g., a reporter gene), either in vitro or in vivo (e.g., in a transgenic animal), using different portions of the GDF-9 regulatory region spanning the 10 kilobase region immediately upstream (i.e., 5') of the coding region of a GDF-9 gene.

Additional aspects of the invention shall be apparent from the detailed description below.

BRIEF DESCRIPTION OF THE DRAWINGS

FIG. 1 shows a comparison between the nucleotide sequence of the first 376 base pairs of the region immediately 5' of the transcription initiation site of the mouse (mGDF) (SEQ ID NO:2) and human (hGDF) (SEQ ID NO:3) GDF-9 genes. The sequences are oriented 3' to 5' so that the numbering of nucleotides (+1) begins after the ATG translation start codon. As shown, the overall identity between the mGDF and hGDF sequences is 71.3%.

FIG. 4 shows the results of a northern analysis of tissues from a different transgenic mouse line (compared to FIG. 3) containing the 3.3 kilobase GDF-9-GFP construct shown in FIG. 2. Tissues were hybridized with a $^{35}$S-labeled anti-GFP probe. Both the ovary and the testis show marked GFP mRNA accumulation.

FIG. 6 shows a map comparing the 5' flanking sequences of the mouse GDF-9 gene and the mouse ZP3 gene (Lira et al. (1993) *Mol. Repro. Dev.* 36:494–499). Conserved regions, such as the E-Box at bases −182 and −183, respectively, are shown.

DETAILED DESCRIPTION OF THE INVENTION

Figure 2:
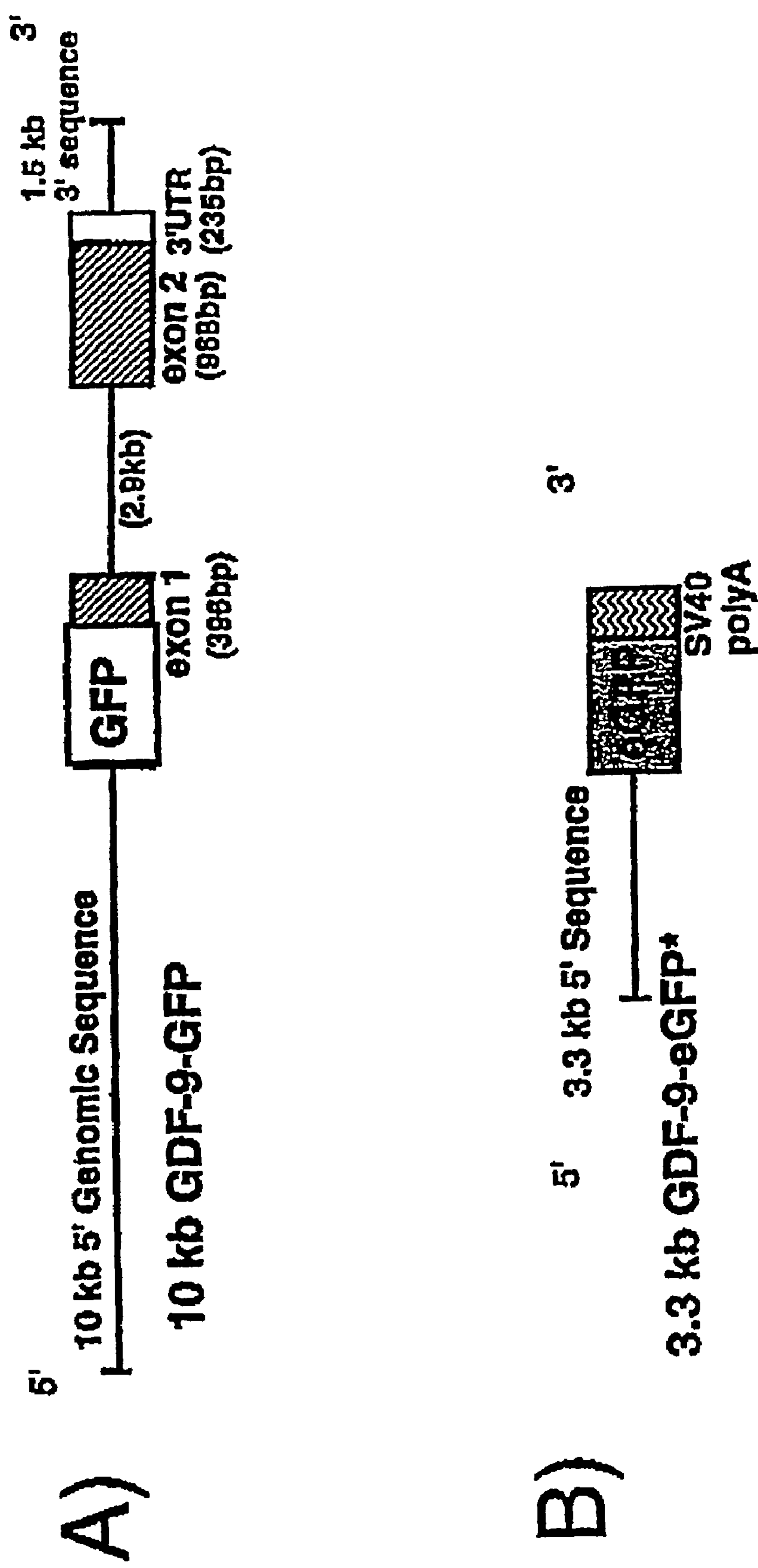
FIG. 2 shows a map of two GDF-9 transgenes constructed and utilized for site-specific expression studies. In panel A, the GFP transgene includes the genomic 10 kilobase 5'-flanking region immediately upstream of the start codon for GDF-9 operatively linked to the green fluorescence protein (eGFP) gene. In panel B, the GFP transgene includes the genomic 3.3 kilobase 5'-flanking region immediately upstream of the start codon for GDF-9 operatively linked to the enhanced green fluorescence protein (eGFP) gene. The eGFP gene is a version of the GFP gene that has been optimized for mammalian expression and contains an optimized translation start site.

The present invention is based on the identification and isolation of GDF-9 regulatory elements which can be used to control (e.g., upregulate or down-regulate) expression of selected genes in specific tissues (e.g., oocyte, testis and other tissues in which GDF-9 is naturally expressed).

Definitions

As used herein, the terms defined below shall have the following meanings.

An "isolated polynucleotide" refers to a polynucleotide (e.g., a DNA) removed from its natural sequence context. The isolated polynucleotide can be any polynucleotide that is capable of being transcribed or translated in a cell. The isolated polynucleotide can be, for example, cloned (genomic or cDNA clone) into a vector. Except as noted hereinafter, standard techniques for cloning, DNA isolation, amplification and purification, for enzymatic reactions involving DNA ligase, polymerase, restriction endonucleases and the like and various separation techniques are those known and commonly employed by those skilled in the art. A number of standard techniques are described in: Maniatis et al. (1982) Molecular Cloning, Cold Spring Harbor Laboratory, Cold Spring Harbor, N.Y.; Wu (ed.) (1979) Meth. Enzymol 68; Wu et al. (Eds.) (1983) Meth. Enzymol. 100 & 101; Grossman and Moldave (eds.) (1980) Meth. Enzymol. 65; Miller (ed) (1972) Exp. Mol. Genetics, Cold Spring Harbor, N.Y.; Old and Primrose (1981) Principles of Gene Manipulation, Univ. of Cal. Press, Berkeley; Schlief and Wensink (1982) Practical Methods in Molecular Biology; Glover (ed) 1985 (DNA Cloning, Vols. I and II, IRL Press, Oxford, UK; Sellow and Hollaender (1979) Genetic Engineering: Principles and Methods, Vols I, Plenum Press, NY; which are incorporated by reference in their entirety herein. Abbreviations, where employed, are those deemed standard in the field and commonly used in professional journals such as those cited herein.

The term "derived from", as it is used herein, refers to an actual or theoretical source or origin for isolated polynucleotides of the invention. For example, a polynucleotide that is "derived from" a particular polynucleotide (e.g., a GDF-9 gene) will be identical or highly homologous in nucleotide sequence to a relevant portion of the reference polynucleotide (e.g., a GDF-9 gene) molecule. Thus, for example, a polynucleotide that is "derived from" the first 10 kilobases or 3.3 kilobases of DNA immediately 5' of the coding sequence of a GDF-9 gene may correspond in nucleotide sequence to all or a portion of the 10 kilobase or 3.3 kilobase upstream sequence of wild-type GDF-9 gene. Isolated polynucleotides of the invention which are "derived from" GDF-9 genes (e.g., the region immediately 5' of the transcription initiation site) also include those which have been modified by insertion, deletion or substitution of one or more nucleotides but which retain substantially the same activity or function.

A DNA "coding sequence", "coding region", or a "sequence encoding" a particular protein is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, cDNA from eukaryotic mRNA, genomic DNA sequences from eukaryotic (e.g., mammalian, animal, avian etc.) sources, and even synthetic DNA sequences. A transcription termination sequence will usually be located 3' to the coding sequence.

A "GDF-9 gene", as used herein, refers to a GDF-9 gene (e.g., a cloned genomic gene or a cDNA), including its untranscribed upstream and downstream regions and transcribed, untranslated regions from any species which naturally expresses GDF-9. For example, the nucleotide sequence for the genomic human GDF-9 gene is available at Genbank accession #AC004500. A "nonhuman GDF-9 gene", as used herein, refers to a GDF-9 gene (e.g., a cloned genomic gene or a cDNA), including its untranslated regulatory regions, from any species excepting human (e.g., avian, sheep, porcine, ovine, bovine). For example, the nucleotide sequence for the mouse GDF-9 gene is provided in U.S. Pat. No. 5,821,056, the complete contents of which are incorporated by reference herein.

The terms "regulatory element", "control element" and "regulatory sequence" are used interchangeably herein, and refer to a nucleic acid which, when operably linked to a gene, effects ("modulates") or causes transcription and/or expression levels of the gene in a cell. Such genetic regulatory elements are well known in the art and include, for example, promoters, enhancers and other cis-acting sequences involved in the binding of transcription factors/repressors. For example, a "promoter" is a regulatory element to which an RNA polymerase can bind, permitting the transcription and subsequent translation of an operatively linked coding sequence. Regulatory elements include both positive and negative ("repressors") regulators of transcription.

The term "promoter", as used herein, refers to a nucleotide sequence generally located adjacent to the 5' end of a structural gene that is involved in the initiation of transcription. Promoters contain DNA sequence elements that ensure proper binding and activation of an RNA polymerase, influence where transcription will start, and affect the level of transcription. The term "repressor" refers to a regulatory element generally located adjacent to the 5' end of a structural gene that is involved in the repression of the initiation of transcription, frequently by binding RNA polymerase, or by binding factors interfering with the processivity or binding of RNA polymerase to the gene transcription start site. Further, specific regulatory sequences within or adjacent to promoters that are functional in the regulation (induction and repression) of gene expression responsive to stimuli or specific chemical species may also be present. The sizes of these regulatory elements are variable. In many cases, regulatory activity can be within approximately 500 bases to 3000 bases of sequence in the 5' direction (or upstream) to the site of transcription initiation. However, sequences out to approximately 4000 base pairs 5' to the structural gene have been implicated in the regulation of gene expression of certain genes. These control elements, however, may be located even further upstream of the structural gene under their control.

The majority of regulatory elements control initiation of transcription and processivity of the RNA polymerase in one direction only, so in order to be under the control of a regulatory element, a structural gene must usually be located downstream (in the 3' direction) of the element and in the correct orientation with respect to the element. The distance between the element and the structural gene is believed to be an important factor in gene expression level. One or several genes may be under the control of a single element or, conversely, one or more regulatory elements may control a single structural gene.

Environmental factors such as temperature, light, and oxygen tension, and chemical species such as nutrients, metabolites, heavy metal ions and steroids have been found to regulate gene expression. Factors that induce expression as well as factors that repress expression of genes have been identified. The exact mechanism of regulation by such signals or stimuli is likely to be complex, involving multiple protein interactions. By analogy to previous mechanistic studies of regulation, however, regulatory control is expected to involve changing the ability of RNA polymerase to bind to DNA sequences in the promoter region. One possible mechanism is the binding of regulatory protein to a DNA sequence at or near the position of binding of RNA polymerase to enhance or prevent transcription. A second possible mechanism is direct or indirect interaction of a signal (inducer or repressor) molecule with RNA polymerase, itself, to change its specificity for recognition and binding to a DNA sequence of the promoter. In either case, specific sequence(s) within the promoter would be involved in the mechanism of regulation, the presence within a promoter region of one or several sequences can be important to the regulation of promoter activity.

"Expression" of a gene requires both transcription of DNA into mRNA and the subsequent translation of the mRNA into protein products.

The term "reporter gene", as used herein, refers to a gene encoding a protein which is readily quantifiable or observable. Because gene regulation usually occurs at the level of transcription, transcriptional regulation and promoter activity are often assayed by quantitation of gene products. For example, promoter regulation and activity has often been quantitatively studied by the fusion of the easily assayable *E. Coli* lacZ gene to heterologous promoters (Casadaban and Cohen (1980) J. Mol. Biol. 138:179–207). The structural gene for chloramphenicol acetyl transferase (CAT) and green fluorescence protein (GFP) are other genes commonly used to detect activity of a promoter or other regulatory sequence.

The term "tissue-specific expression", as it is used herein, refers to a limited or characteristic pattern of gene expression among cell types. In other words, expression of a gene is observed in certain tissues of an organism but not in other tissues. For example, "oocyte-specific" expression of a gene denotes that that gene is expressed in the oocyte and optionally limited other tissues, but is not expressed in all tissues (e.g., globally).

A "vector" is a replicon, such as a plasmid, phage, or cosmid, to which another DNA segment may be attached so as to bring about the replication of the attached segment.

An "expression vector" means any DNA vector (e.g., a plasmid vector) containing the necessary genetic elements for expression of a desired gene, including a promoter region of the present invention. These elements are "operably linked" to the gene, meaning that they are located at a position within the vector which enables them to have a functional effect on transcription of the gene. The regulatory elements need not be contiguous with the coding sequence, so long as they function to direct the expression thereof. Thus, for example, intervening untranslated yet transcribed sequences can be present between a promoter and the coding sequence and the promoter can still be considered "operably linked" or "in operable linkage to" the coding sequence.

A cell has been "transformed" by exogenous DNA (e.g., a transgene) when such exogenous DNA has been introduced inside the cell membrane. Exogenous DNA may or may not be integrated into the chromosomal DNA comprising the genome of the cell. With respect to eukaryotic cells, though, a stably transformed cell is one in which the exogenous DNA has become integrated into the chromosome such that it is inherited by daughter cells though chromosome replication.

A "host cell" is a cell that has been transformed, or is capable of transformation, by an exogenous nucleic acid molecule.

A "transgene" refers to a nucleic acid which is introduced into a cell. Typically, the transgene is integrated into the genome of the cell following introduction. The transgene can encode a protein which is not expressed in the cell or which is expressed in the cell at low levels or in defective form.

A "transgenic animal" is an animal carrying in its cells at least one transgene. For example, the transgenic animal can contain in its cells a transgene corresponding to a gene of another species which has been introduced into the germline of the animal, such that the introduced gene is present in all somatic and germline cells.

Identification and Isolation of GDF-9 Regulatory Sequences

GDF-9 regulatory sequences can be identified and isolated from a variety of sources including mammalian and avian genomic and cDNA libraries. They can also be prepared (e.g., synthesized) from a variety of known and sequenced GDF-9 genes. For example, the nucleotide sequence for the genomic human GDF-9 gene is available at Genbank accession #AC007400. The nucleotide sequence for the ovine GDF-9 gene is published in Bodensteiner et al. (1999) *Biol. Reprod* 60:381–386 and is accessible at Genbank accession #AF078545. The nucleotide sequence for the mouse GDF-9 gene is published in Incerti et al. (1994) *Biochimica et Biophysica Acta* 122:125–128.

In one embodiment of the invention, GDF-9 regulatory sequences are obtained from the first 10 kilobases of DNA immediately 5' of the coding sequence of a GDF-9 gene, such as the mouse GDF-9 gene. In another embodiment, the GDF-9 regulatory sequences are derived from the first 3.3 kilobases of DNA immediately 5' of the transcription initiation site of a GDF-9 gene. For example, the sequences can be derived from the 3.3 kilobase regulatory region from the mouse GDF-9 gene (mGDF-9) having the nucleotide sequence of SEQ ID NO:1. In another embodiment, the GDF-9 regulatory sequences are derived from the first 300 base pairs of DNA immediately 5' of the transcription initiation site of a GDF-9 gene. In still another embodiment, the GDF-9 regulatory sequences are derived from the region from 3.3 kilobases to 10 kilobases 5' of the transcription initiation site of a GDF-9 gene. In another embodiment, the GDF-9 regulatory sequences are derived from the untranscribed 3' flanking region of a GDF-9 gene, or from a transcribed, untranslated region of a GDF-9 gene (e.g., an intron which is spliced out from the GDF-9 mRNA during processing).

Isolation and cloning of GDF-9 regulatory sequences can be performed using standard techniques well-known in the art, such as those discussed above and in the examples provided below.

The observed tissue-specific expression of growth differentiation factor 9 (GDF-9) demonstrates that there is one or more control element(s) for the GDF-9 gene which is permissive to GDF-9 expression in certain tissues, such as the oocyte (among other tissues) while it is repressive to this expression in other cell types.

As part of the present invention, it was discovered that the region immediately 5' of the transcription initiation site of the GDF-9 gene (spanning the first 10 kilobases) contains not only one or more regulatory elements (e.g., promoters) specifically directing the expression of GDF-9 in certain tissues, such as oocytes, testicular cells, and the hypothalamus, but also one or more repressor elements specifically inhibiting expression of GDF-9 in testicular cells. Accordingly, in one embodiment, the present invention provides isolated GDF-9 regulatory sequences derived from each of the first 10, 3.3, or 0.3 kilobases of DNA immediately 5' of the transcription initiation site of a nonhuman GDF-9 gene. Other embodiments include isolated polynucleotide molecules spanning each of the regions 3.3 kilobases, 10 kilobases, and 3.3–10 kilobases immediately 5' of the transcription initiation site of a nonhuman GDF-9 gene.

GDF-9 regulatory elements derived from these regions, and other untranscribed upstream and downstream regions, and transcribed, untranslated regions (e.g., introns) of GDF-9 genes, which regulate tissue-specific gene expression, can be identified by examining these regions for the presence of particular sequences which effect transcription and/or expression of a gene when the gene is operatively linked to the sequences. For example, it was found as part of the present invention that the aforementioned 0.3 3.3, and 10 kilobase regions from the region immediately 5' of the mouse GDF-9 transcription initiation site promote oocyte-specific expression of a reporter gene. It was also found that the 3.3 kilobase region promotes expression of a reporter gene in testis, but that the 10 kilobase region does not. This finding demonstrates the presence of a testis-specific repressor element in the region from 3.3 to 10 kilobases immediately 5' of the transcription initiation site of the mouse GDf-9 gene. Further mapping of such promoter and repressor elements can be achieved by similarly testing smaller fragments of these regions to define the particular sequences involved in gene regulation.

Other functional mapping techniques also may be employed to further characterize and identify specific GDF-9 regulatory sequences. For example, nucleotide bases within these regions (e.g., the 0.3, 3.3 or 10 kilobase fragments of the 5' region) can be mutated by, for example site-directed mutagenesis, to add, delete or change one or more bases (e.g., 6–12 bases), followed by testing the mutated regulatory sequences for activity either in vitro (e.g., by microinjection or transfection) or in vivo (e.g., in a transgenic animal) to see what functional effect the mutation had. From this information, nucleotide bases required for function (e.g., upregulation or downregulation) of the regulatory element can be determined. For example, if upon mutating a small (e.g., 6–12 base pair) segment of the 5' region of a GDF-9 gene, transcription levels of a reporter gene operatively linked to the 5' region are diminished, then this small region can be concluded to be involved in promoting transcription (e.g., by binding to one or more transcription factors). Transcription factors that bind cis-acting regulatory elements may also interact with each other. Therefore, multiple reporter constructs can be developed and tested for the interaction between their potential cis-elements and such binding proteins using the assays described herein.

Accordingly, in another embodiment, the invention provides a method for identifying GDF-9 regulatory elements by operatively linking various portions (e.g., overlapping portions) of the region immediately 5' of the transcription initiation site (e.g., the first 10 kilobases) of a GDF-9 gene, or other untranslated (e.g., 3') regions of a GDF-9 gene, to a coding sequence (e.g., of a reporter gene), and comparing expression levels and patterns in vivo (e.g., in a transgenic animal) or in vitro (e.g., in an oocyte) among these constructs. Methods for preparing such constructs and for operatively linking genes (e.g., within plasmid vectors) to such regulatory sequences are well known in the art. For example, a first expression construct which includes a portion of the 10 kilobase region immediately 5' of the transcription initiation site of a GDF-9 gene, in operative linkage with a reporter gene, can be introduced, e.g., by microinjection, into an oocyte or other tissue which naturally expresses GDF-9, followed by measurement of the activity of the reporter gene (e.g., by Northern blot). A second expression construct, including a different portion of the 10 kilobase region immediately 5' of the transcription initiation site of the same GDF-9 gene, also in operative linkage with the same reporter gene, can then be introduced into an oocyte, and activity of the reporter gene again measured. Upon comparison of the activities of the reporter genes controlled by the two different GDF-9 regulatory regions, a conclusion about the regulatory function (e.g., repressor or promoter activity) of the utilized portion of the region immediately 5' of the transcription initiation site can be drawn.

Alternatively, regulatory regions of GDF-9 genes can be identified by comparing untranscribed upstream and downstream regions, and transcribed, untranslated regions of a GDF-9 gene with 5' and 3' sequences from other known genes, for example, which are expressed is a similar tissue-specific pattern and, therefore, which may contain related or homologous regulatory elements. For example, as part of the present invention, the first 300 bases of the mouse GDF-9 gene immediately 5' of the transcription initiation site mouse GDF-9 gene was compared to the same region from the mouse ZP3 gene (Millar et al. (1991) *Molec. Cell. Biol.* 11:6197–6204), which is expressed predominantly in the oocyte, and homology was observed in certain regions. One such region is the E-box (CANNTG, where N is any nucleotide base) located approximately 200 bases upstream of the transcription start site. The E-box in the ZP3 gene is a conserved DNA element which has been shown to bind basic helix-loop-helix transcription factors, many of which are tissue-specific (Liang et al. (1997) *Development* 124: 4939–4947).

Similarly, sequences derived from the untranscribed upstream and downstream regions, and transcribed, untranslated regions of a GDF-9 gene can be compared to sequences in a global gene database (e.g., GenBank) using computer programs well-known in the art to identify homologous regulatory sequences from other known genes.

In addition, DNA probes can be synthesized corresponding to a portion of an untranscribed or transcribed regulatory region of a GDF-9 gene, such as the mouse GDF-9 gene described herein, and used to screen for homologous sequences from other GDF-9 genes using, e.g., in situ hybridization. For example, DNA probes corresponding to portions of first 3.3 kilobases of DNA (SEQ ID NO:1) immediately 5' of the mouse GDF-9 transcription start site can be generated and used to screen for homologous sequences which hybridize to the probes, preferably under high stringency conditions.

Accordingly, GDF-9 regulatory sequences of the invention include homologous sequences from other species and sequences which have been altered but retain a high percentage of sequence identity. Preferred GDF-9 regulatory sequences have at least about 50% homology, more preferably at least about 60% homology and most preferably at least about 70–99% homology with regulatory sequences derived from the first 10, 3.3 or 0.3 kilobases of DNA upstream of the mouse GDF-9 gene transcription start site. Homology refers to sequence similarity between two nucleic acid molecules. Homology can be determined by comparing a position in each sequence which may be aligned for purposes of comparison. When a position in the compared sequence is occupied by the same base, then the molecules are homologous at that position. A degree of homology between sequences is a function of the number of matching or homologous positions shared by the sequences.

Using the aforementioned methods, tissue-specific regulatory elements derived from GDF-9 genes can be identified and then synthesized, cloned or otherwise isolated. Accordingly, other embodiments of the invention include isolated tissue-specific (e.g., oocyte-specific or testis-specific) promoter and enhancer elements derived from a GDF-9 gene. Other embodiments include isolated tissue-specific repressor elements derived from a GDF-9 gene. These regulatory elements can be operatively linked to a gene of interest, directing or repressing expression of the gene in a tissue-specific manner. For example, repression of certain functionally active genes in the testis is desirable, and the GDF-9 repressor element has the ability to direct the repression of such genes in testicular cells.

Expression Vectors and Transfection of Cells with GDF-9 Regulatory Sequences

In another embodiment, the invention provides an expression vector which includes one or more of the aforementioned GDF-9 regulatory elements in operative linkage with a gene of interest, such that expression of this gene is under control of the GDF-9 regulatory element. In one embodiment, the regulatory element is derived from the 10 kilobases of the region immediately 5' of the transcription initiation site of a GDF-9 gene. Any gene that expresses a protein of interest may be employed in the methods of the invention. Similarly, the invention may be used to repress expression of any gene desired to be downregulated in a specific tissue. Examples of such genes include GDF-9 itself, growth factors, genes encoding antigens to tumors or pathogens, and reporter genes. However, this is not intended to be a limiting list.

When employed in the context of heterologous structural genes, the precise optimal location of the control sequences of the invention with respect to the transcription initiation site may vary. Generally, the control sequences are placed up to about 300 nucleotides or more from a transcription initiation site. However, in other embodiments, control sequences are located within 150 nucleotides of the transcription initiation site. Therefore, to employ regulatory elements of the invention in the context of a heterologous gene, the regulatory elements can simply be inserted into an expression construct upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the GDF-9 control sequences. Alternatively, one may desire to simply employ the TATA sequences normally associated with the heterologous gene. Such TATA sequences are most desirably located between about 20 and 30 nucleotides upstream of transcription initiation.

GDF-9 regulatory sequences of the present invention, whether positive, negative, or both, may be cloned into such expression vectors in the form of multiple units, in numerous various combinations and organizations, in forward or reverse orientations, and the like. Moreover, in the context of multiple unit embodiments and/or in embodiments which incorporate both positive and negative control units, there is no requirement that such units be arranged in an adjacent head-to-head or head-to-tail construction in that the improved regulation capability of such multiple units is conferred virtually independent of the location of such multiple sequences with respect to each other. There is no requirement that each unit comprise the same positive or negative element. All that is required is that such sequences be located upstream of and sufficiently proximal to a transcription initiation site for the gene of interest.

The control sequences of the present invention may be beneficially employed in the context of any heterologous gene, with or without additional homologous or heterologous control or promotion sequences. The present invention encompasses GDF-9 gene promoters and other regulatory sequences which function in the induction or repression of GDF-9 expression in response to tissue-specific factors (e.g., transcription factors) that induce and repress GDF-9 expression. A GDF-9 promoter-GFP reporter construct was used in the instant invention, however any suitable reporter gene may be used to measure the activity of the GDF-9 promoter.

In yet another embodiment, the invention provides a cell, preferably a cell which naturally expresses GDF-9 (e.g., an oocyte cell line), stably transformed with one or more of the aforementioned GDF-9 5'-flanking region polynucleotides, or with one of the expression vectors previously described. For example, the cell can be transformed in vitro or in vivo with the isolated GDF-9 regulatory region which, in certain embodiments, can be inserted into a particular locus of the cells genome. Methods for such site-specific insertion of transgenes into chromosomal DNA are well known in the art and include, for example, the mammalian Cre/lox system (Sauer et al. (1998) *Methods* 14:381–392) or homologous recombination (see e.g., U.S. Pat. No. 5,614,396). By targeting the regulatory sequences to locations upstream of endogenous genes, expression of these genes can be controlled accordingly (e.g., upregulated or downregulated).

Alternatively, the GDF-9 control elements of the invention can be introduced into cells in operational linkage with a transgene. Introduction of the GDF-9-transgene construct into a host cell will result in expression or repression of the transgene, depending on the element or combination of elements contained within the construct. In specific embodiments, this expression or repression occurs specifically in oocytes or testicular cells. For example, an expression vector containing the aforementioned 3.3 kilobase mouse GDF-9 promoter element in operative linkage with a gene encoding luciferase will cause oocyte and testis-specific expression of luciferase upon introduction into oocytes or testicular cells. Similarly, transformation of a testicular cell with an expression vector containing the previously described 3.3 to 10 kilobase region from the mouse GDF-9 5' UTR, or derivatives thereof, in operative linkage with the luciferase gene will cause testis-specific repression of the luciferase gene.

Another embodiment of the present invention provides the utilization of the previously described GDF-9 regulatory elements to identify proteins and molecules involved in the regulation of GDF-9 transcription and translation. In one embodiment, one or more GDF-9 regulatory elements, such as a GDF-9 promoter, is operatively linked to a reporter gene, such as the green fluorescent protein gene. Factors or compounds can then be tested using this construct for their ability to effect expression levels of the reporter gene compared to a control. Such screening methods and how to perform them are well known to those of ordinary skill in the art. Suitable reporter assays include, for example, CAT assays and luciferase assays. The invention is not restricted to these suggested screening methods. Any method known in the art may be employed whereby compounds can be tested for their ability to increase or stimulate the expression of a reporter gene compared to that of a control reporter gene, (e.g., the SV40 β-galactosidase reporter gene). Effects of the test compound are determined by changes in reporter gene activity.

Transcription factors that bind to these specific regulatory sequences can be characterized using gel mobility shift assays and these transcription factors can be cloned using these specific sequences as probes in screening expression libraries. After these transcription factors have been identified, they too, may be used as targets for identifying other inhibitors. For example, these transcription factors can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the transcription factors. Such transcription factor-binding proteins are also likely to act as modulators, e.g., inhibitors of GDF-9 expression.

Uses of the Invention

GDF-9 regulatory sequences of the present invention can be used to selectively express GDF-9 and other gene products of interest in the oocyte, testis, hypothalamus, placenta and other tissues in which GDF-9 mRNA is naturally transcribed. GDF-9 regulatory sequences may also be used to repress GDF-9 expression and other gene products (e.g., tumor antigens) in specific tissues, such as the testis.

Tissue-specific expression of genes, particularly in the oocyte, can be used to develop treatments for infertility, or conversely, can be used for purposes of contraception, either through the selective expression of a nonfertility factor in oocytes, or through the selective repression of a fertility factor in testicular cells.

GDF-9 regulatory sequences of the invention also can be used to develop transgenic animals in which one or more genes are specifically expressed or repressed in the oocyte, testis, and hypothalamus. Techniques for generating such transgenic animals are now well known in the art.

As previously discussed, GDF-9 regulatory sequences of the present invention also can be used to identify other homologous tissue-specific regulatory elements. Accordingly, an important aspect of this invention is the utility of the disclosed elements and genetic regions as probes for the detection of similar regulatory sequences and regions in other genomes, or elsewhere within a given genome.

GDF-9 regulatory sequences of the invention also can be used to selectively express or repress desired gene products in germ cells. For example, the Cre/lox site-specific recombination system previously described herein can be used in oocytes (e.g., from mouse), or in both male and female germ cells (e.g., from mouse), to target GDF-9 repressor elements upstream of selected genes so that they inhibit expression of the genes, thereby creating germ cell-specific knockouts. This ability is particularly important for genes that cause early death in conventional knockouts, since the reproductive function of the eliminated genes cannot be assessed in that situation.

As previously discussed, GDF-9 regulatory sequences of the invention also can be used to identify and to refine germ-cell promoter elements. Small polynucleotide molecules based upon DNA sequence from identified GDF-9 promoter region(s) can be labeled and used as probes for the identification of other regions similar in sequence in a given genome. The functionality of such regions as promoters of expression in germ cells can be assessed using methods disclosed in this invention. GDF-9 regulatory sequences of the invention also can be used as reagents for the further identification of testicular cell repressor elements. For example, small polynucleotide molecules based upon DNA sequence from the 3.3 kb–10 kb GDF-9 testis-specific repressor region discussed herein can be labeled and used as probes for the identification of other regions similar in sequence in a given genome. The functionality of such regions as repressors in the testis can be assessed using methods disclosed in this invention. GDF-9 regulatory sequences of the invention also can be used to identify somatic cell repressor elements that are similar to the aforementioned testicular cell repressor element for the GDF-9 gene.

GDF-9 regulatory sequences of the invention also can be used as reagents for use in gene therapy. For example, GDF-9 promoter and repressor elements can be included in somatic gene therapy vectors. In the case of the GDF-9 testis-specific repressor element, inclusion in such a vector permits the expression of a desired protein (such as a toxin or a drug) in all tissues in which the vector was incorporated (generally any rapidly dividing cell) with the exception of testicular cells. This permits the male germline cells to survive treatments of this kind, thus protecting male fertility.

GDF-9 regulatory sequences of the invention also can be used to generate "marked" germ cells. By permitting the directed expression of a reporter gene specifically to certain tissues, such as oocytes or testicular cells, the present invention permits the generation of germline cells including a recognizable or measurable protein marker. For example, expression of green fluorescent protein in oocytes under the direction of the GDF-9 promoter results in a population of oocytes which each contain the characteristic fluorescent protein. Other such reporter genes are well known in the art. Such cell lines can be used for testicular or ovarian chimeric analysis, or for germ cell kinetic studies. Also, they could be easily separated from somatic cells by flow-sorting technology without the necessity of antibody staining, permitting the generation of pure germ cell populations for library construction, in vitro culture or fertilization.

This invention is further illustrated by the following examples that should not be construed as limiting. The contents of all references, patents and published patent applications cited throughout this application are incorporated herein by reference.

EXEMPLIFICATION

1. Cloning of the GDF-9 Genomic Locus

A GDF-9 cDNA probe was amplified using PCR primers based on the human GDF-9 published sequence in a PCR reaction from mouse ovary RNA. This mouse cDNA probe was used to screen a mouse genomic λ FIX II library from mouse 129SvEv (Stratagene). Seven independent phages were identified, purified and screened by Southern blot analysis. Two of the GDF-9 genes containing phage were subcloned and further characterized. One of these two phage, B/S4, contained 10 kb of sequence 5' to the beginning of GDF-9 exon I, GDF-9's entire coding region GDF-0 exon I (387 bp), intron (2.9 kb), and exon II (909 bp), and −1 kb of 3' genomic sequence (Incerti et al. 1994).

2. Construction of GDF-9 Transgenes a) Alteration of the GDF-9 Initiation Codon to a BamHI Site A 700 bp PstI fragment which contains −400 base pairs of GDF-9 exon I was subcloned into pBluescript SK+ (Stratagene). Two polymerase chain reactions (PCR) were performed on this subclone using one vector specific primer and one primer that matched the region of GDF-9's initiation codon with several mismatches. Primer sequences were as follows (mismatched bases are underlined new BamHI site is in italics): GDF9-E1: 5'TTCTTC AAG GGATCC CACTTTCCCAG3' (SEQ ID NO:4) and GDF9-E2: 5'CTGGGAAGTG GGATCC CTGGAAGAA3'(SEQ ID NO:5).

b) Introduction of Mutated GDF-9 Regulatory Region into pE22

The new BamHI site was used to reassemble the 700 base pair region from the two PCR products. This region was sequenced to ensure that there were no PCR errors. In a several step process, the full 15.5 kilobase genomic locus initially cloned in B/S4 was reassembled to include the unique BamHI site and mutated initiation codon (plasmid pE22).

c) Construction of GDF-9 Transgene 1 (10 kb-GDF-9-GFP) (see FIG. 2)

Plasmid pE22 was linearized with BamHI and the 700 base pair coding region of green fluorescent protein was inserted. A −17.5 kilobase fragment (SalI/NotI) was injected into pronuclei of fertilized 1-cell embryos. Mice in which transgene integration had occurred were identified by Southern blot analysis of tail DNA using both a GFP probe and a GDF-9 exon II probe. Two transgene-positive founders were generated.

d) Construction of GDF-9 Transgene 2 (3.3 kb-GDF-9-GFP) (See FIG. 2)

Plasmid pE22 was cut with EcoRV and BamHI to generate a 3.3 kilobase piece immediately 5' to the initiation codon. This was ligated immediately upstream of the ATC of enhanced green fluorescent protein cDNA (Clontech) containing its own SV40 polyadenylation sequence. A −4.0 kilobase fragment was injected as above and 6 independent transgene-positive lines were identified using the eGFP coding region probe.

3. Transgene Expression Analysis

Total RNA was isolated from brain, heart, lung, stomach, liver, spleen, kidney, small intestine, skin, uterus, ovary and testes using RNA Stat 60 (Leedo Medical, Houston, Tex.) according to manufacturer's instructions, from each transgene-positive line. RNA was electrophoresed on a 1.2% agarose/formaldehyde gel, transferred to nylon membrane, probed with eGFP or eGFP coding region $^{32}$P-labeled probe and analyzed autoradiographically as previously described (Dube et al, 1998). Cellular localization of transgene expression was conducted by in situ hybridization. Briefly, ovaries from transgene-positive mice and transgene-negative (wild-type) mice were fixed overnight in 4% paraformaldehyde (PFA), processed and embedded in paraffin. 5 micron thick sections were cut, dewaxed, rehydrated and post-fixed in 4% PFA. Sections were pretreated in 50 μg/ml proteinase K and acetic anhydride in 0.1 M triethanolamine. Sections were hybridized overnight at 55° C. with either $^{35}$S labeled sense or antisense riboprobe for FGP or eGFP. Sections were washed in 5×SSC/50% formamide and 0.1×SSC at 65° C. Slides were dipped in NTBZ liquid photographic emulsion (Kodak) and exposed at 40° C. for 3–10 days. After development, signal was visualized by dark field microscopy.

Figure 5:
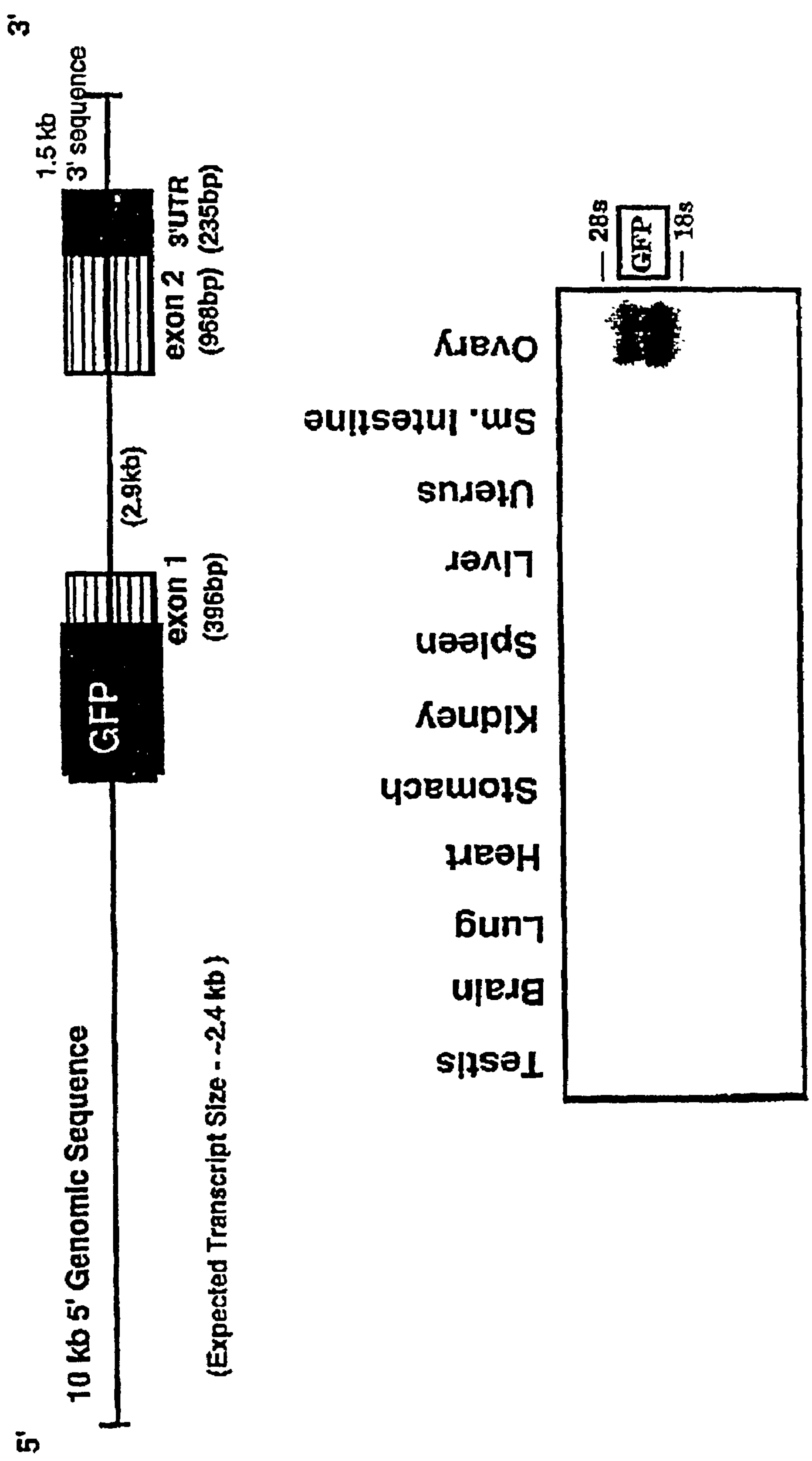
FIG. 5 shows a northern analysis of tissues from a transgenic mouse line containing the 10 kilobase GDF-9-GFP construct shown in FIG. 2. Tissues were hybridized with an anti-GFP probe. Only the ovary shows marked GFP mRNA accumulation.

Of the two lines of transgenic mice incorporating the first GDF-9-GFP construct (containing 10 kb of the 5' flanking sequence), in situ hybridization and multi-tissue northern blot analysis of mouse tissues demonstrated marked ovary-specific expression in the first line (FIG. 5). The presence of signal in other tissues in the second line was most likely due to elements present at the site of transgene integration.

Figure 3:
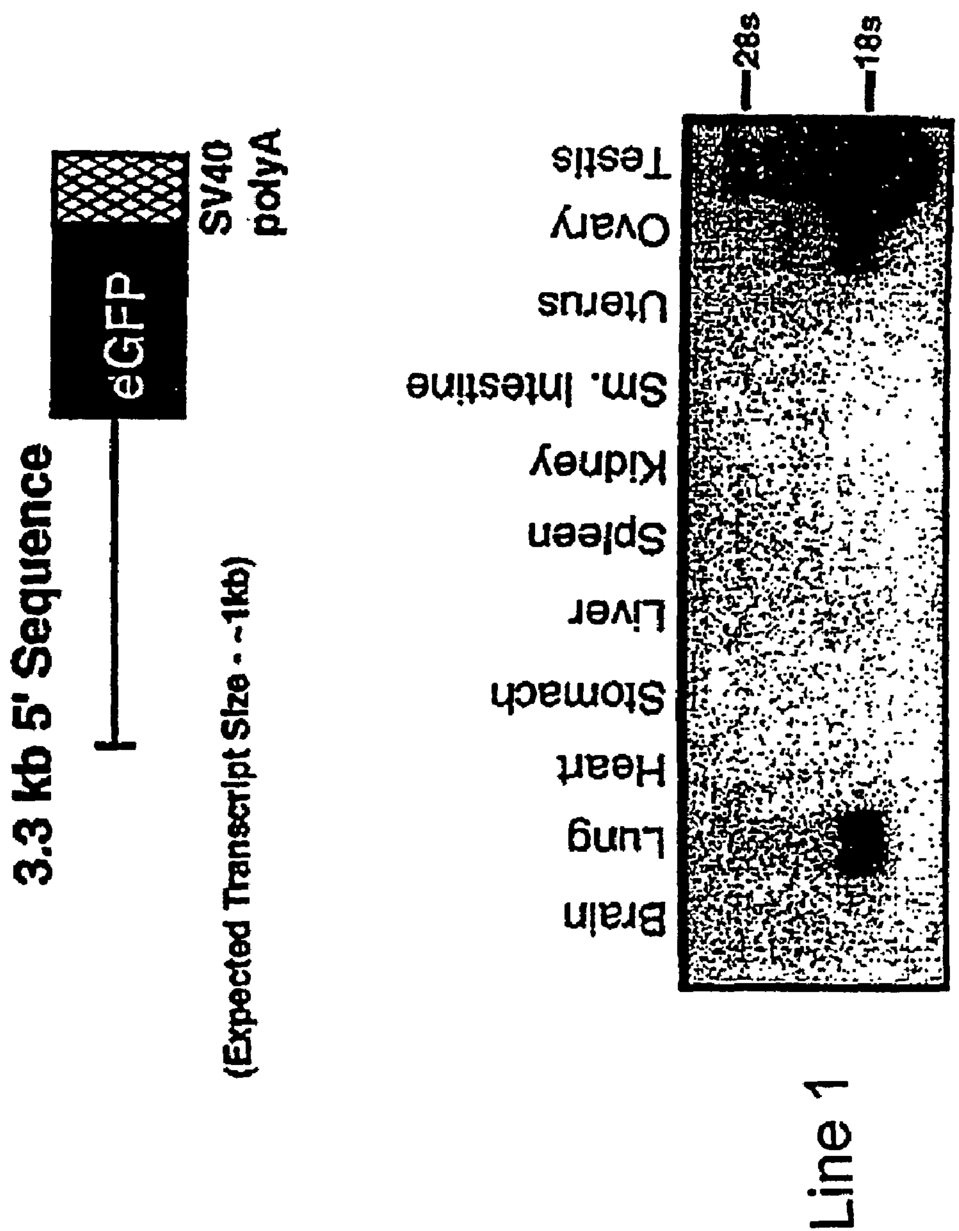
FIG. 3 shows a northern analysis of tissues from a transgenic mouse line containing the 3.3 kilobase GDF-9-GFP construct shown in FIG. 2. Tissues were hybridized with a $^{35}$S-labeled anti-GFP probe. Both the ovary and the testis show marked GFP mRNA accumulation.

Six lines of mice carrying the second GDF-9-GFP construct were established. This construct contains only 3.3 kb of 5' flanking sequence linked to an enhanced version of GFP. Two of the six mouse lines showed oocyte-specific expression in the ovary by in situ hybridization. By multi-tissue northern blot analysis, signal was detected in the ovary, and to a much higher level in the testis (FIGS. 3 and 4). In situ hybridization for eGFP in the testis demonstrated that expression was restricted to the germ cells, specifically, primary spermatocytes through round spermatid stages. Similar studies in the ovary determined that expression is limited to the oocytes. One of the two lines also had a strong signal in the lung, most likely attributable to integration of the transgene near a strong lung-specific promoter or enhancer.

4. Sequence Analysis of GDF-9 Upstream Region

Figure 7:
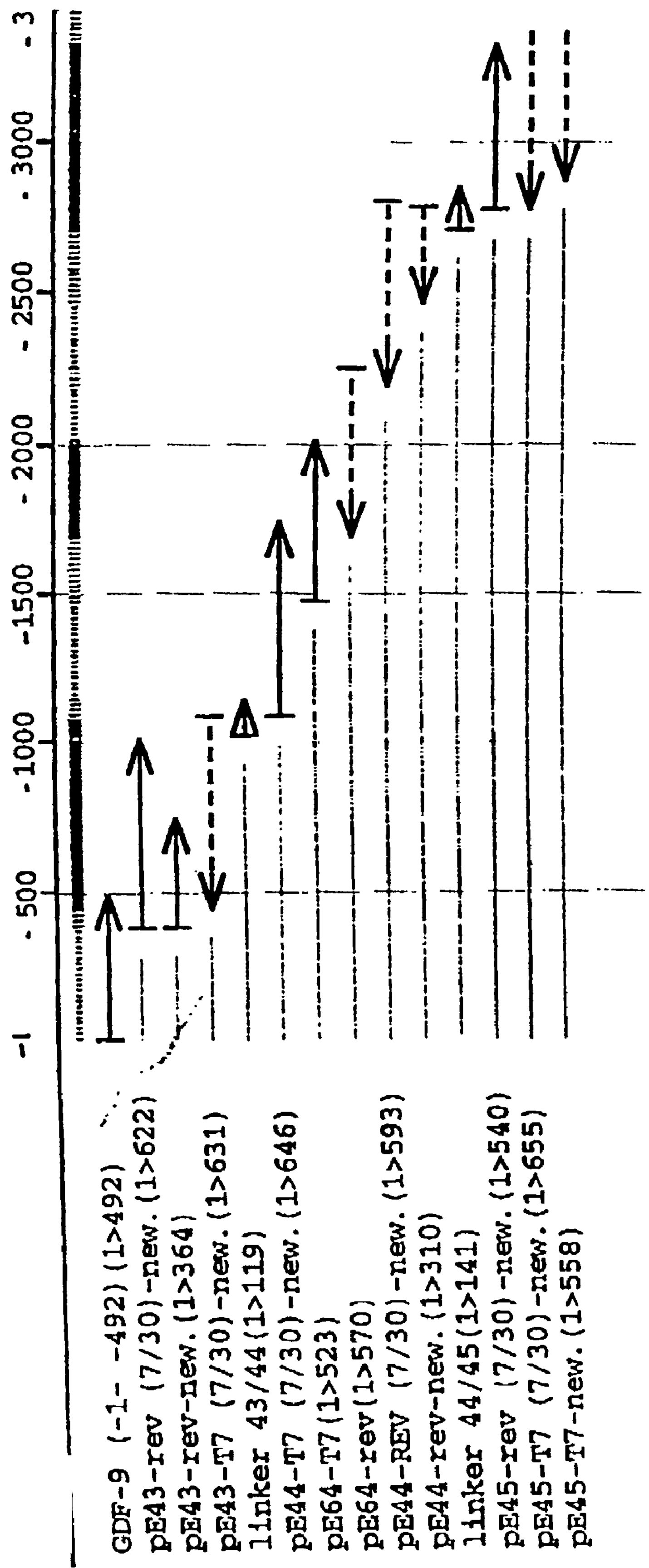
FIG. 7 shows the sequencing strategy for the first 3.3 kilobases of the 5'-flanking sequence of the mouse GDF-9 gene. The numbering (+1) is relative to the transcription start site (ATG).

The 3.3 kb region present in GDF-9 transgene 2 was subcloned (FIG. 7) and sequenced with 1×–3× coverage with vector primers by a standard dye termination method using fluorescently labeled dideoxy-nucleotide triphosphates and an ABI automatic sequence. Raw sequences were assembled using Lasergene and DNA Strider sequence analysis software. The complete sequence is shown in SEQ ID NO:1. Potential transcription factor binding sites and regulatory sequences were identified using Signal Scan (available through the University of Singapore home page). The human genome sequencing project sequenced the human GDF-9 within a much larger P1 clone from human chromosome 5 (Genbank accession #AC004500). Regions of sequence identity between human and mouse 5' sequences (See FIG. 1) were revealed using a local alignment program LFASTA and LALIGN (GCG sequence analysis software). Promoter regions of other oocyte-expressed genes were scanned manually for interesting transcription factor binding sites conserved between mouse and human GDF-9 (particularly GATA-1 and E-boxes). To identify potentially relevant sequences a comparison with the 5' flanking region of the mouse zona pellucida 3 (mZP3) gene was made. Transgene studies using just the first 280 bp of 5' flanking sequence from mZP3 demonstrated that this region is sufficient to direct oocyte expression. Sites shown to be critical for mZP3 oocyte expression, including the E-box, are also found within the first 300 bp of 5' flanking sequence from mGDF-9 (see FIG. 6).

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated polynucleotide comprising a portion of the mouse GDF-9 gene capable of regulating expression of an operably linked gene in oocytes, wherein the portion comprises the first 10 kilobases of DNA immediately 5' of the transcription start site of the GDF-9 gene.

2. An isolated polynucleotide comprising a portion of the mouse GDF-9 gene capable of regulating expression of an operably linked gene in oocytes or testis, wherein the portion comprises the first 3.3 kilobases of DNA immediately 5' of the transcription start site of the GDF-9 gene.

* * * * *

UNITED STATES PATENT AND TRADEMARK OFFICE

CERTIFICATE OF CORRECTION

PATENT NO. : 7,227,013 B1
APPLICATION NO. : 10/018638
DATED : June 5, 2007
INVENTOR(S) : Martin Matthew Matzuk et al.

It is certified that error appears in the above-identified patent and that said Letters Patent is hereby corrected as shown below:

** Insert --Related U.S. Application Data:

Provisional Application No.: 60/080,108, filed on April, 1998.--**

Signed and Sealed this

Twenty-third Day of October, 2007

JON W. DUDAS
*Director of the United States Patent and Trademark Office*